(12) United States Patent
Gu et al.

(10) Patent No.: US 10,271,745 B2
(45) Date of Patent: Apr. 30, 2019

(54) MONOLITHIC INTEGRATED EMITTER-DETECTOR ARRAY IN A FLEXIBLE SUBSTRATE FOR BIOMETRIC SENSING

(71) Applicant: QUALCOMM Incorporated, San Diego, CA (US)

(72) Inventors: Shiqun Gu, San Diego, CA (US); Matthew Michael Nowak, San Diego, CA (US); Kenneth Kaskoun, La Jolla, CA (US); Eugene Dantsker, San Diego, CA (US); Russel Allyn Martin, Menlo Park, CA (US)

(73) Assignee: QUALCOMM Incorporated, San Diego, CA (US)

( * ) Notice: Subject to any disclaimer, the term of this patent is extended or adjusted under 35 U.S.C. 154(b) by 375 days.

(21) Appl. No.: 15/186,347

(22) Filed: Jun. 17, 2016

(65) Prior Publication Data

US 2017/0360316 A1 Dec. 21, 2017

(51) Int. Cl.
*A61B 5/1455* (2006.01)
*A61B 5/024* (2006.01)
(Continued)

(52) U.S. Cl.
CPC ...... *A61B 5/02433* (2013.01); *A61B 5/14532* (2013.01); *A61B 5/14552* (2013.01);
(Continued)

(58) Field of Classification Search
CPC . A61B 5/0205; A61B 5/1455; A61B 5/14551; A61B 5/14552; A61B 5/14532;
(Continued)

(56) References Cited

U.S. PATENT DOCUMENTS

2009/0112071 A1\* 4/2009 LeBoeuf ............ A61B 5/14552
600/301
2010/0113948 A1 5/2010 Yang et al.
(Continued)

FOREIGN PATENT DOCUMENTS

EP 2898822 A1 7/2015
WO 2014168718 A1 10/2014
(Continued)

OTHER PUBLICATIONS

International Search Report and Written Opinion—PCT/US2017/031154—ISA/EPO—dated Aug. 4, 2017.

*Primary Examiner* — Eric F Winakur
*Assistant Examiner* — Chu Chuan Liu
(74) *Attorney, Agent, or Firm* — Bala Ramasamy; Kilpatrick Townsend & Stockton (57) ABSTRACT

Examples of monolithic integrated emitter-detector array in a flexible substrate for biometric sensing and associated devices and methods are disclosed. One disclosed example device includes a flexible substrate; a first array of emitters embedded in the flexible substrate, the first array of emitters configured to emit first electromagnetic (EM) signals; a first array of detectors embedded in the flexible substrate, the first array of detectors configured to detect reflections of the first EM signals; a first scanning circuit coupled to the first array of emitters, the first scanning circuit configured to selectively activate individual emitters of the first array of emitters; and a first sensing circuit coupled to individual detectors of the first array of detectors, the first sensing circuit configured to receive a detection signal from at least one of the detectors of the first array of detectors.

26 Claims, 5 Drawing Sheets

(51) Int. Cl.
*A61B 5/145* (2006.01)
*A61B 5/00* (2006.01)

(52) U.S. Cl.
CPC ............ *A61B 5/681* (2013.01); *A61B 5/6823* (2013.01); *A61B 5/6824* (2013.01); *A61B 5/6828* (2013.01); *A61B 5/7278* (2013.01); *A61B 5/742* (2013.01); *A61B 5/7475* (2013.01); *A61B 5/14551* (2013.01); *A61B 2560/0214* (2013.01); *A61B 2560/0475* (2013.01); *A61B 2562/04* (2013.01); *A61B 2562/046* (2013.01); *A61B 2562/164* (2013.01)

(58) Field of Classification Search
CPC ....... A61B 5/681; A61B 5/72; A61B 5/02433; A61B 5/742; A61B 5/6823; A61B 5/6824; A61B 5/7475; A61B 5/7278; A61B 5/6828
See application file for complete search history.

(56) References Cited

U.S. PATENT DOCUMENTS

| 2011/0112379 | A1* | 5/2011 | Li | A61B 5/14552 600/300 |
| 2012/0165759 | A1* | 6/2012 | Rogers | A61B 5/6867 604/264 |
| 2013/0261415 | A1 | 10/2013 | Ashe et al. | |
| 2014/0275891 | A1 | 9/2014 | Muehlemann et al. | |
| 2014/0288390 | A1* | 9/2014 | Hong | A61B 5/02416 600/301 |
| 2015/0157219 | A1 | 6/2015 | Lee et al. | |

FOREIGN PATENT DOCUMENTS

| WO | 2015000997 A1 | 1/2015 |
| WO | 2015046624 A1 | 4/2015 |
| WO | 2015056007 A1 | 4/2015 |

* cited by examiner

MONOLITHIC INTEGRATED EMITTER-DETECTOR ARRAY IN A FLEXIBLE SUBSTRATE FOR BIOMETRIC SENSING

BACKGROUND

It is often desirable for a user to be aware his/her bodily function measurements. Recently, many individuals wear small portable devices capable of measuring their heart rate (HR) and other physiological information. One of the techniques used by these devices to measure heart rate is photoplethysmography (PPG). Many of the small portable fitness devices are wearable electronics that are typically package in the form of a watch (e.g., smart watch), activity monitoring band (e.g., worn on the wrist), etc.

However, these devices typically have one or two light sources that illuminate light into the user's skin and one or two detectors to measure the reflected light in order to obtain the PPG measurement. In the everyday course of the user's activities, however, these wrist-worn devices are susceptible to rotation around the wrist (e.g., when a user is walking, etc.) Even a small rotation of the device around the user's wrist can cause decrease in accuracy by a factor of two. This is due to the amount of measured light because the arteries in the portion where a user typically wears a wrist-worn device are rather sparse. Thus, these wrist-worn devices may not always be able to obtain the most accurate PPG measurement due to having only a small number of light sources and detectors which may not always be located at the optimum location around the user's wrist due to rotations of the device around the user's wrist during the course of their everyday life.

BRIEF SUMMARY

Various examples are described for monolithic integrated emitter-detector array in a flexible substrate for biometric sensing. For example, one disclosed device includes a flexible substrate; a first array of emitters embedded in the flexible substrate, the first array of emitters configured to emit first electromagnetic (EM) signals; a first array of detectors embedded in the flexible substrate, the first array of detectors configured to detect reflections of the first EM signals; a first scanning circuit coupled to the first array of emitters, the first scanning circuit configured to selectively activate individual emitters of the first array of emitters; and a first sensing circuit coupled to individual detectors of the first array of detectors, the first sensing circuit configured to receive a detection signal from at least one of the detectors of the first array of detectors.

In another example, one disclosed system includes a wearable housing; a processor and a non-transitory computer-readable medium disposed within the wearable housing, the processor in communication with the non-transitory computer-readable medium and configured to execute program code stored in the non-transitory computer-readable medium; a monolithic sensor in communication with the processor and configured to provide sensor signals to the processor, the sensor comprising: a flexible substrate; a first array of emitters embedded in the flexible substrate, the first array of emitters configured to emit first electromagnetic (EM) signals; a first array of detectors embedded in the flexible substrate, the first array of detectors configured to detect reflections of the first EM signals; a first scanning circuit coupled to the first array of emitters, the first scanning circuit configured to selectively activate individual emitters of the first array of emitters; and a first sensing circuit coupled to individual detectors of the first array of detectors, the first sensing circuit configured to receive a detection signal from at least one of the detectors of the first array of detectors.

In a further example, one disclosed method includes for each emitter of an array of emitters embedded in a flexible substrate, each emitter configured to emit an electromagnetic (EM) signal: activating the emitter, receiving a detector signal from one or more detectors of an array of detectors corresponding to the activated emitter, the array of detectors embedded in the flexible substrate, and determining a quality of the received detector signal; selecting an emitter and corresponding detector having a high quality of the determined qualities; deactivating all emitters of the plurality of emitters; activating the selected emitter; and determining biometric information based at least in part on a detector signal received from the corresponding detector.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 1A-2 show example flexible sensing devices including monolithic integrated emitter-detector arrays in a flexible substrate for biometric sensing;

DETAILED DESCRIPTION

Examples are described herein in the context of monolithic integrated emitter-detector arrays in a flexible substrate for biometric sensing. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Illustrative Example of a Monolithic Integrated Emitter-Detector Array in a Flexible Substrate for Biometric Sensing In one illustrative example, a sensor for sensing biometric information includes a flexible substrate, such a plastic substrate. Such a substrate allows the sensor to wrap around, or otherwise conform, to a portion of a person's body, such as a wrist or arm. Embedded within the substrate are a number of emitters that emit light in one or more wavelengths. In addition, a number of detectors are also embedded within the substrate to detect light reflected off of the portion of the person's body.

In this example, the sensor is a part of a wearable device to be worn around a user's wrist. The emitters are embedded within the flexible substrate in a rectangular array to allow illumination of a large portion of the user's wrist. The detectors are also embedded within the flexible substrate in a rectangular array that corresponds with the array of emitters. Thus, when the emitters emit light, the light will reflect off of the user's wrist and be detected by one or more of the detectors.

The arrays of emitters and detectors are connected to a processor within the wearable device. The processor is able to selectively activate the emitters, individually or in groups, and then receive information from the detectors. However, because the wrist has a sparse layout of blood vessels near the surface of the skin, some of the emitters will not illuminate any blood vessels, or will only poorly illuminate a nearby blood vessel, and corresponding detectors will not detect useful biometric information. Thus, the processor attempts to optimize the use of the emitters and detectors to identify the emitters that result in the best quality detector readings, and discontinue activating the other emitters. To do so, the processor selective activates emitters one at a time and obtains signals from one or more detectors. The processor evaluates each detector signal to determine whether the signal provides useful biometric information or not, and identifies the emitters that, when activated, resulted in the best biometric information. The processor then adjusts its configuration to use the identified emitters to obtain biometric information and to deactivate the other emitters. Over time, the processor may continue to evaluate the received biometric information and may re-optimize emitter selection over time. For example, if the wearable device moves on the user's wrist, different emitters may result in better biometric information. Thus, the processor may periodically re-optimize its emitter usage, or may do so when the quality of the detected biometric information drops below a threshold. Further, by deactivating one or more emitters, the wearable device may reduce its power consumption, thereby increasing its battery life.

This illustrative example is not intended to be in any way limiting, but instead is intended to provide an introduction to the subject matter of the present application. For example, the illustrative example above is described with respect to an autonomous car; however, the present application is not limited to such an environment, but may be used in any suitable environment. Other examples of monolithic integrated emitter-detector arrays in a flexible substrate for biometric sensing are described below.

Figure 1A:
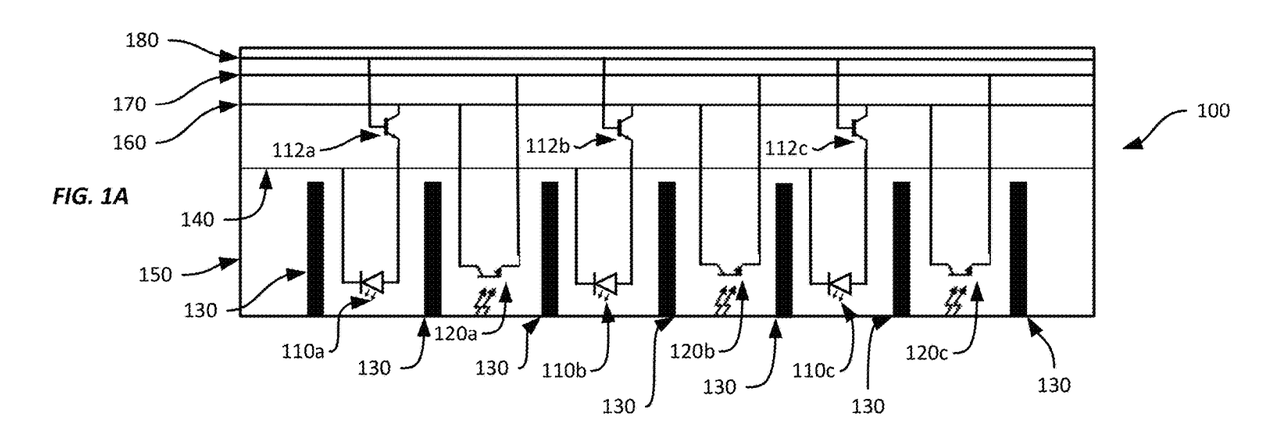

Referring now to FIG. 1A, FIG. 1A shows a cross-section of an example monolithic integrated emitter-detector array in a flexible substrate for biometric sensing. In this example, the sensing device 100 has a flexible substrate 150 in which are embedded several emitters 110*a-c* and several detectors 120*a-c*, which are separated by optical shielding 130. Each emitter 110*a-c* is connected to a power source by a switch 112*a-c*, which allows each emitter 110*a-c* to be independently activated of the other emitters. In this example, a processor is connected to each switch 112*a-c* and toggles a switch to activate the corresponding emitter(s). For example, each switch may be connected to the processor via a switch matrix circuit to enable individual addressing of each switch. In some examples, pins on the processor may each be connected to a corresponding switch via an individual wire thus allowing one pin on the processor to change the state of the corresponding switch.

In different examples, the flexible substrate 150 may be a polymer material, such as a fluoropolymer/polyimide copolymer, an acrylic-based material, a polyester material, a polyimide material, a polyethylene naphthalate material, a polyetherimide material, a fluoropolymer, or a copolymer comprising two or more of the foregoing materials. In some examples, the substrate may have a single layer or may have more than one layers. Multiple layers of substrates of the same or different types may be bonded using suitable adhesives. In some examples, the flexible substrate 150 may have a thickness between approximately 12 to 127 microns (+/−5 microns).

In this example, the switches 112*a-c* comprise a transistor coupling a power source, provided by wire 160, to a respective emitter 110*a*, which, in this example, are each also coupled to an electrical ground 140. The transistors are configured to operate in a saturation mode to gate power on or off to the respective emitter. For example, a signal may be provided to the switch via a scanning circuit 180, which as described above may comprise a switch matrix or a discrete wire running from a processor to the switch. However, in some examples, the switches 112*a-c* may allow for different settings to affect an intensity or type of signal emitted by the corresponding emitter 110*a-c*. Further, while in this example each switch 112*a-c* is coupled to only one emitter, in some examples, a switch 112*a-c* may be coupled to and configured to activate/deactivate multiple emitters.

In this example, the emitters 110*a-c* are light emitting diodes (LEDs) that emit red light in the visible spectrum when activated. However, other color LEDs may be employed, such as orange or green. For example, an orange LED may be advantageous for sensing biometric information on people having darker skin, while red LEDs may be more advantageous for sensing biometric information on people having lighter skin. In some examples, the emitters 100*a-c* may emit electromagnetic (EM) signals in wavelengths outside the visible spectrum; however, for purposes of this description EM signals include visible light and infrared radiation. For example, the following table illustrates wavelengths, in nanometers (nm), of EM radiation that correspond to different colors of light and infrared radiation:

| Color | Wavelength |
| --- | --- |
| Infrared | 751-1,000,000 nm |
| Red | 620-750 nm |
| Orange | 591-620 nm |
| Yellow | 571-590 nm |
| Green | 496-560 nm |
| Blue | 451-495 nm |
| Violet | 380-450 nm |

It should be understood, however, the ranges given above are not intended to be exact for all examples. For example, each color range may extend +/−10 nm or +/−2% beyond what is recited in the table above.

In some examples, different types of emitters 110*a-c* may be employed. For example, a first set of emitters may be configured to output red light, a second set of emitters may be configured to output orange light, and a third set of emitters may be configured to output green light. In one such example, each set of emitters may have a separate scanning circuit, which may allow a processor to separately and independently activate or deactivate emitters of one kind or another. However, in some examples, all three sets of emitters may be coupled to the same scanning circuit. Further, it should be understood that while this example includes three sets of emitters configured to output specific EM signals, different numbers of emitters, sets of emitters, or EM signal configurations may be employed in different examples according to this disclosure.

In some examples, emitters may be selected based on a desired frequency of emitted EM signal. For example, red light or near infrared radiation may be desirable, such as for sensing a level of blood oxygen saturation. In some examples, green light may be desirable for sensing a pulse or a pulse rate. Further, in some examples, a sensing device may include different kinds of emitters, such as to allow sensing of different kinds of biometric information with a single sensing device.

The sensing device 100 also includes several detectors 120a-c. The detectors 120a-c are arranged to correspond with one or more emitters 110a-c. In this example, the detectors 120a-c comprise silicon photodiodes, however, other suitable detectors include photoresistors, photodiodes, amorphous silicon, and organic CMOS. The detectors 120a-c are configured to detect EM signals emitted by one or more of the emitters 110a-c. For example, based on the selection of emitters and the EM signals emitted by each, detectors 120a-c should be selected to match such selected emitters. For example, if emitters that emit red light are selected, at least one detector should be selected that can detect red light and emit a detector signal indicating the detection of red light. Further, detectors 120a-c should be located in sufficient proximity to corresponding emitters to allow the detector to detect reflected EM signals emitted by the emitters.

In this example, each of the detectors 120a-c is configured to output one or more sensor signals in response to detecting an EM signal. In some examples, the detectors 120a-c may output a saturation signal to that provides a binary indication of whether an EM signal was detected, e.g., either an EM signal was detected or not. In some examples, however, the detectors 120a-c may output a signal indicating information about the detected EM signal, such as intensity or color. For example, a detector 120a may be configured to detect orange light and may output an voltage or current based on the intensity of the detected EM signal, or the color of the detected signal.

As can be seen in this example, each detector 120a-c is connected to a sensing circuit 170 that is configured to carry detector signals, such as to a processor or other device. In this example, each detector 120a-c is connected to a discrete wire dedicated to the respective detector 120a-c, however, in other examples each detector 120a-c may be coupled to a wire matrix configured to provide row and column identification as well as a detector signal from the respective detector 120a-c. In some examples, different types of detectors 120a-c may be employed. For example, a first set of detectors may be configured to detect red light, a second set of detectors may be configured to detect orange light, and a third set of detectors may be configured to detect green light. In one such example, each set of detectors may have a separate sensing circuit, which may allow a processor to separately and independently receive detecting signals from one kind of detector or another. However, in some examples, all three sets of detectors may be coupled to the same sensing circuit. Further, it should be understood that while this example includes three sets of detectors configured to detect specific EM signals, different numbers of detectors, sets of detectors, or EM signal configurations may be employed in different examples according to this disclosure.

In some examples, each detector, or groups of detectors, may be coupled to a sensing circuit by a switch. When the switch is activated, it may allow detector signals generated by the corresponding detector or detectors 120a-c to travel onto the sensing circuit. Thus, like emitters 110a-c, detectors 120a-c may be individually activated or deactivated in a manner similar to that discussed above with respect to emitters. For example, the each detector switch may be connected to a switch matrix (or one of a plurality of switch matrices) to allow a processor to independently activate or deactivate one or more detectors.

Further, the emitters 110a-c and detectors 120a-c are fabricated to provide a monolithic emitter/detector strip in which the emitters 110a-c and detectors 120a-c are fabricated together into a flexible substrate. Advantages according to this disclosure may be realized in part based on the monolithic construction of an array of emitters, an array of detectors, or a combined array of emitters and detectors, rather than using individual emitters and detectors placed within a device.

As is shown in FIG. 1A, the detectors 120a-c are isolated from the emitters 110a-c by optical shielding 130. In this example, the optical shielding 130 comprises an opaque plastic material; however, in some examples, other suitable materials may be used, such as an opaque polymer material, an opaque metallic material, or an opaque portion of the flexible substrate. The optical shielding 130 in this example is arranged and configured to reduce or eliminate direct transmission of EM signals from an emitter 110a-c to a detector 120a-c. Thus, in this example, the detectors 120a-c and optical shielding 130 have been arranged to allow EM signals from one or more of the emitters 110a-c to be reflected from a surface and reach one or more of the detectors 120a-c, however, direct transmission from an emitter to a detector is prohibited by the optical shielding 130. However, in some examples, optical shielding may allow for some reduced amount of EM signals to directly travel from an emitter to a detector, while also allowing reflected EM signals.

Figure 1B:
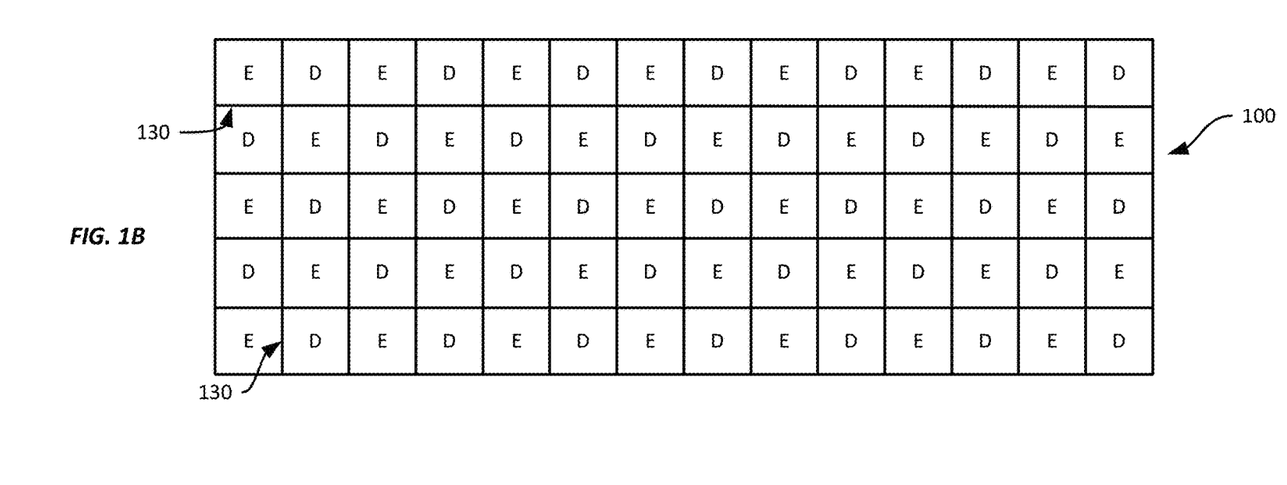

For example, referring to FIG. 1B, FIG. 1B shows a top-down view of an example monolithic integrated emitter-detector array in a flexible substrate for biometric sensing. FIG. 1B illustrates the arrangement of emitters and detectors of the example sensing device 100 shown in FIG. 1A. Emitters are denoted with an "E," while detectors are denoted with a "D." In this example, the emitters and detectors are arranged in a regular "checkerboard" pattern of alternating emitters and detectors in a rectangular pattern. In some examples, other regular patterns may be used, such as hexagonal patterns, triangular patterns, etc. Optical shielding 130 has been arranged in a grid pattern to optically isolate emitters from adjacent detectors. However, as discussed above, other arrangements of emitters, detectors, and optical shielding may be employed.

As shown in FIG. 1B, each emitter is adjacent to a plurality of detectors, and each detector is adjacent to a plurality of emitters. In this example, each emitter is configured to emit the same type of EM signals, e.g., green light, and each detector is configured to detect green light and output a detector signal indicating a detection of green light. However, as discussed above, some examples may employ multiple different types of emitters and detectors.

Figure 2:
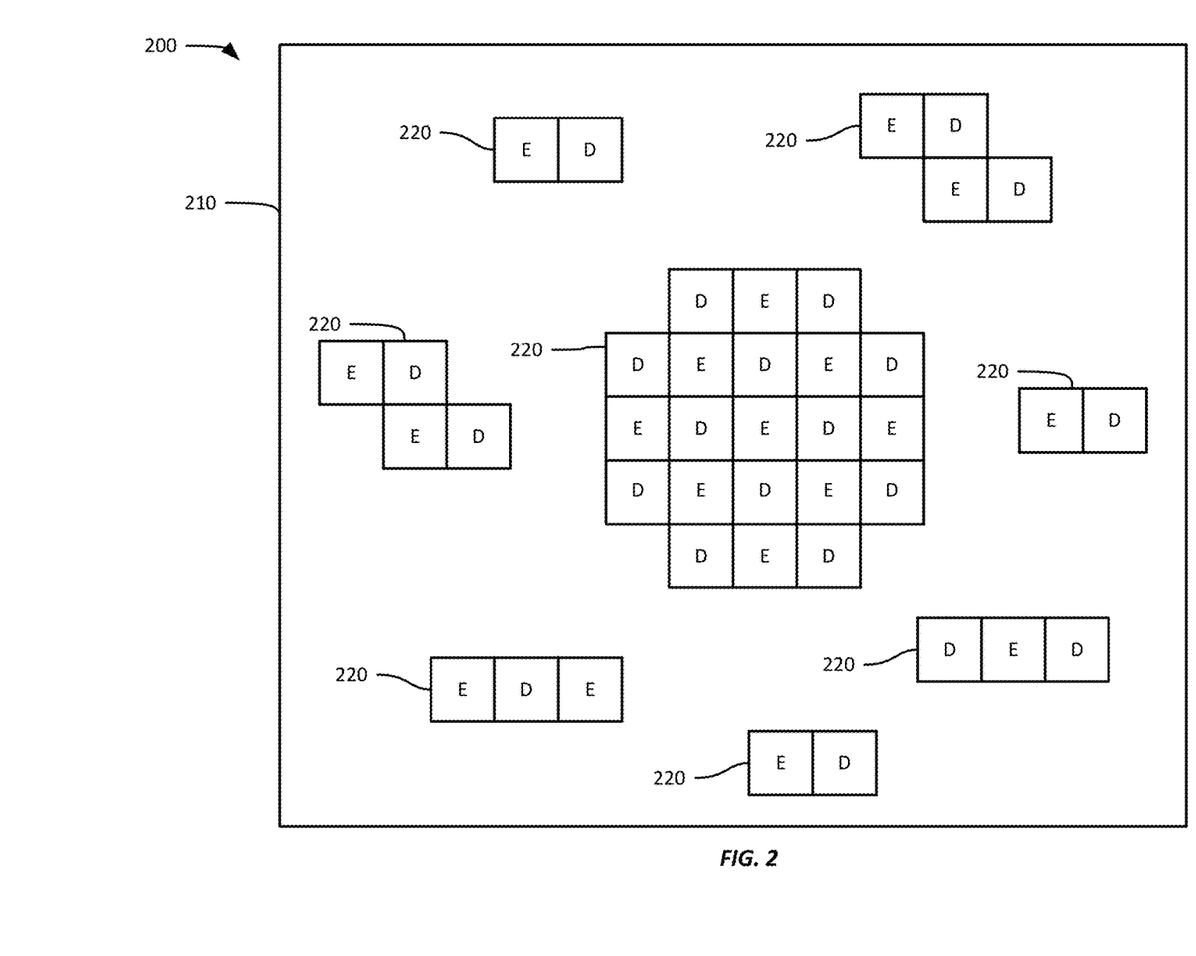

For example, referring to FIG. 2, FIG. 2 shows a top-down view of an example monolithic integrated emitter-detector array in a flexible substrate for biometric sensing. In this example, emitters and detectors, denoted by "E" and "D" respectively, are embedded in a flexible substrate 210 and optically isolated from each other by optical shielding 220. As can be seen, in this example, the arrangement of emitters and detectors is irregular. A number of emitters and detectors have been arranged in a group in the center of the flexible substrate 210, however, a number of other pairs of emitters and detectors have been arranged in other locations in the flexible substrate 210. In some examples, irregular arrangements of emitters and detectors may allow for detection of different biometric information, or may allow for movement of a device, e.g., a wearable device, incorporating the sensing device 200 on a person's body while retaining the ability to sense biometric information. For example, a person may wear a wristband incorporating an example sensing device according to this disclosure. Throughout the day, the sensing device may change positions on the person's wrist, but due to the arrangement of emitters and detectors on the sensing device, biometric information may still be sensed. FIG. 2 also illustrates that a single detector may be grouped with multiple emitters, or that multiple detectors may be grouped with a single emitter.

Figure 3:
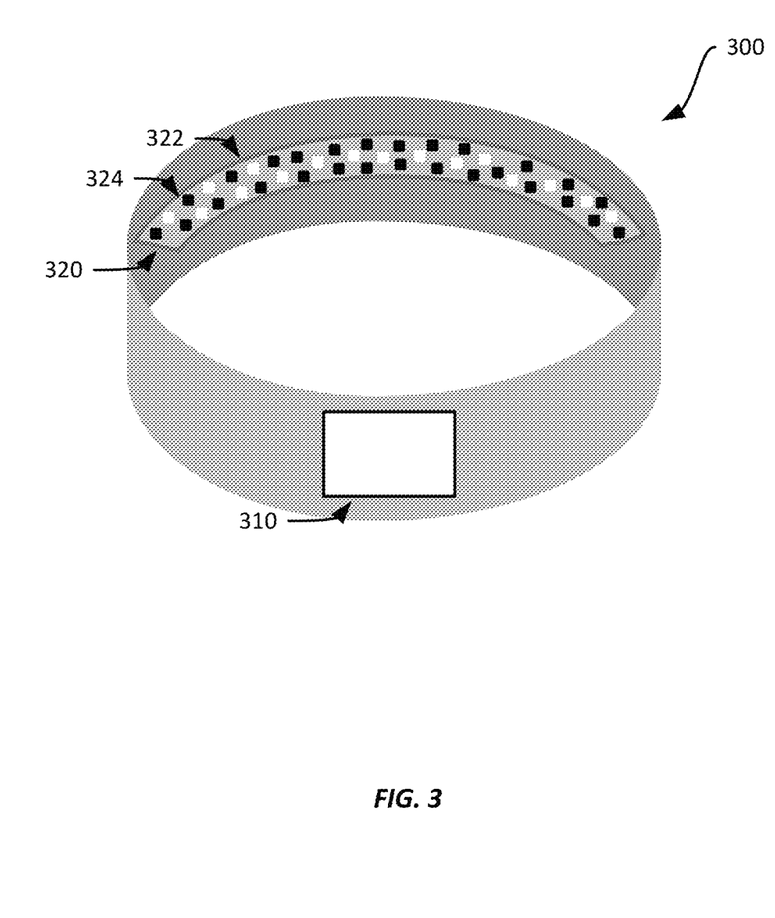
FIG. 3 shows an example wearable device including flexible sensing device.

Referring now to FIG. 3, FIG. 3 shows an example wearable device 300 having an example flexible sensing device 320. The example wearable device 300 includes a computing device 310 and a flexible sensing device 320. In this example, the wearable device 300 is a wristband to be worn on a person's wrist, but could be worn in other locations. The flexible sensing device 320 includes a flexible substrate with several embedded emitters 322 and detectors 324, and optical shielding between the emitters and detectors. As discussed above, each of the emitters 322 is configured to emit EM signals, such as visible light or infrared radiation, and each of the detectors 324 is configured to detect EM signals of the kind emitted by one or more of the emitters 322. The flexible sensing device 320 also includes one or more scanning circuits coupled to the emitters 322, and one or more sensing circuits coupled to the detectors 324. The flexible sensing device 320 also includes optical shielding arranged between the emitters 324 and detectors 322 to reduce or eliminate direct transmission of EM signals from an emitter to a detector.

In this example, the flexible sensing device 320 is disposed within a cavity formed in the wearable device 300 with an adhesive. In some examples, however, the flexible sensing device 320 may be attached to the wearable device 300 in another suitable fashion, such as using screws, rivets, or other fasteners.

The computing device 310 is communicatively coupled to the flexible sensing device 320 and configured to transmit signals to the flexible sensing device 320 to activate and deactivate emitters 322 and receive sensing signals from the detectors 324. The computing device 310 is also configured to determine biometric information from the received signals from the detectors 324. For example, the computing device 310 can determine a pulse rate of the person wearing the wearable device 300, determine a level of oxygen saturation in the person's bloodstream, or determine a level of glucose in the person's bloodstream.

Figure 4:
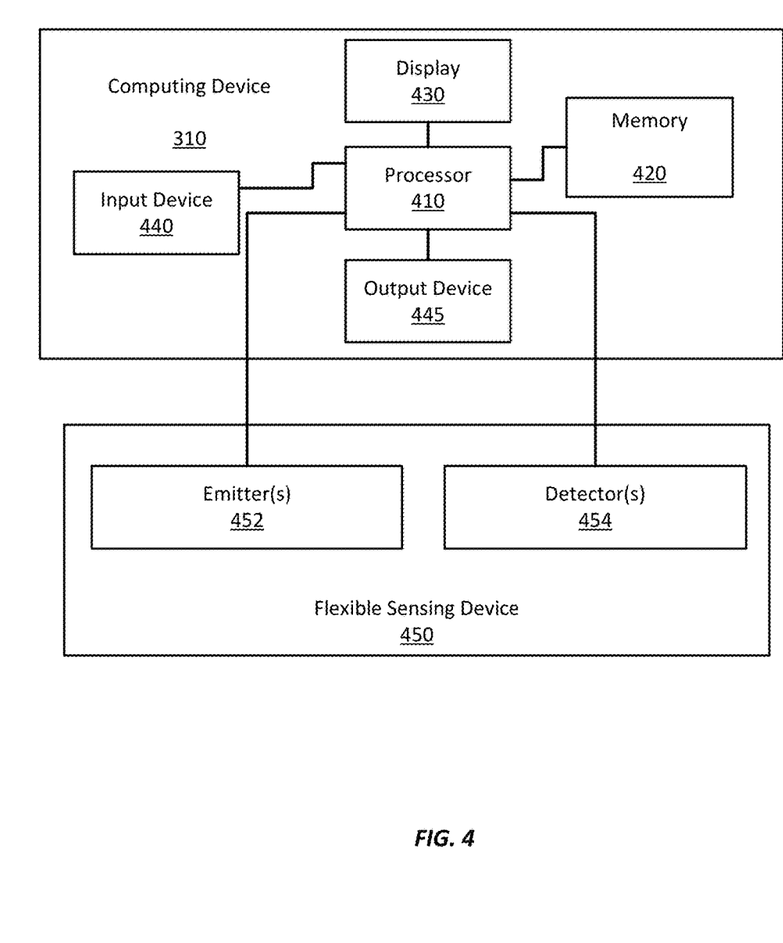
FIG. 4 shows an example computing device for biometric sensing using a flexible sensing device.

Referring now to FIG. 4, FIG. 4 shows an example computing device 310 suitable for use with a monolithic integrated emitter-detector array in a flexible substrate for biometric sensing. The example computing device 310 includes a processor 410, a memory 420, a display device 430, an input device 440, and an output device 445, as well as a power source (not shown) such as a battery. The processor 410 is communicatively coupled to the memory 420 and the display device 430, and is configured to read and execute processor-executable instructions stored in the memory 420. In this example, the display device 420 includes any suitable display device or display devices. For example, a display device 420 may be an LCD display, an LED display, or an OLED display. Further, in some examples, the display device 420 may be a touch-sensitive display device.

Suitable input devices 440 may include a physical manipulatable input device or manipulandum, such as one or more buttons, switches, dials, or sliders. Other input devices may include touch-sensitive input devices, such as capacitive touch sensors, pressure sensors, or strain gages. One or more such touch-sensitive input devices may include a touchscreen or may be disposed on any other surface of the example wearable device to receive user input. However, in some examples, the computing device 310 may not comprise any user input devices 440, but may instead simply provide biometric information to the user.

The computing device 400 may also include one or more output devices 445. Such devices may be configured to communicatively couple to another computing device, such as a medical monitoring device or to a data storage device. For example, the wearable device 300 may be coupled to a patient's skin and connected to a medical computing device, e.g., computing device 310, that monitors pulse rate, blood oxygen levels, blood glucose levels, or other biometric information, and also provides that information via the output device 445 to one or more other medical systems. The wearable device may thus function as a wearable sensing device coupled to an external processing device. In some examples, a user may connect another computing device t other computing device 310, such as to download information from the computing device or to install updated software or settings. Suitable output devices 145 may include a USB interface, an Ethernet interface, an Apple lightning interface, a display interface, a wireless interface such as WiFi, Bluetooth, or near-field communication (NFC), or other suitable output device.

As can be seen in FIG. 4, the example computing device 310 is communicatively coupled to a one or more emitters 452 and one or more detectors 454 of an example flexible sensing device 450, such as shown in FIGS. 1A-3 and described above. As discussed above, the computing device 310 is configured to activate and deactivate one or more of the emitters 452 and receive sensing signals from one or more of the detectors 454. The computing device 310 is further configured to determine biometric information based on the received sensing signals.

In some examples, the computing device 310 is further configured to select an optimal set of emitters for use in obtaining detector signals. For example, depending on the placement of a flexible sensing device 450, or inadvertent movement of the flexible sensing device 450, different emitters may result in better quality detector signals. Thus, the computing device 310 may execute a process to select an optimal set of emitters, and not use other emitters. Such a process may allow for increased battery life as only the subset of optimal emitters may be used during normal operation.

To do so, in this example, the processor 410 selectively activates one or more emitters and obtain corresponding detector signals to identify an emitter or set of emitters that provides the best sensing information for determining biometric information. For example, and as will be discussed in more detail below, the processor 410 may selectively activate and deactivate each emitter individually in succession and analyze the received detector signals to determine a quality of the detector signals. After cycling through each emitter, the computing device 310 determines the best emitter or emitters and only uses the determined emitters for later activation to obtain detector signals. Over time, the processor 410 may re-perform such a process to update the determined emitters, such as to accommodate a different user, a change in position of the flexible sensing device 450, or because a predetermined time has elapsed since a prior optimization process.

Figure 5:
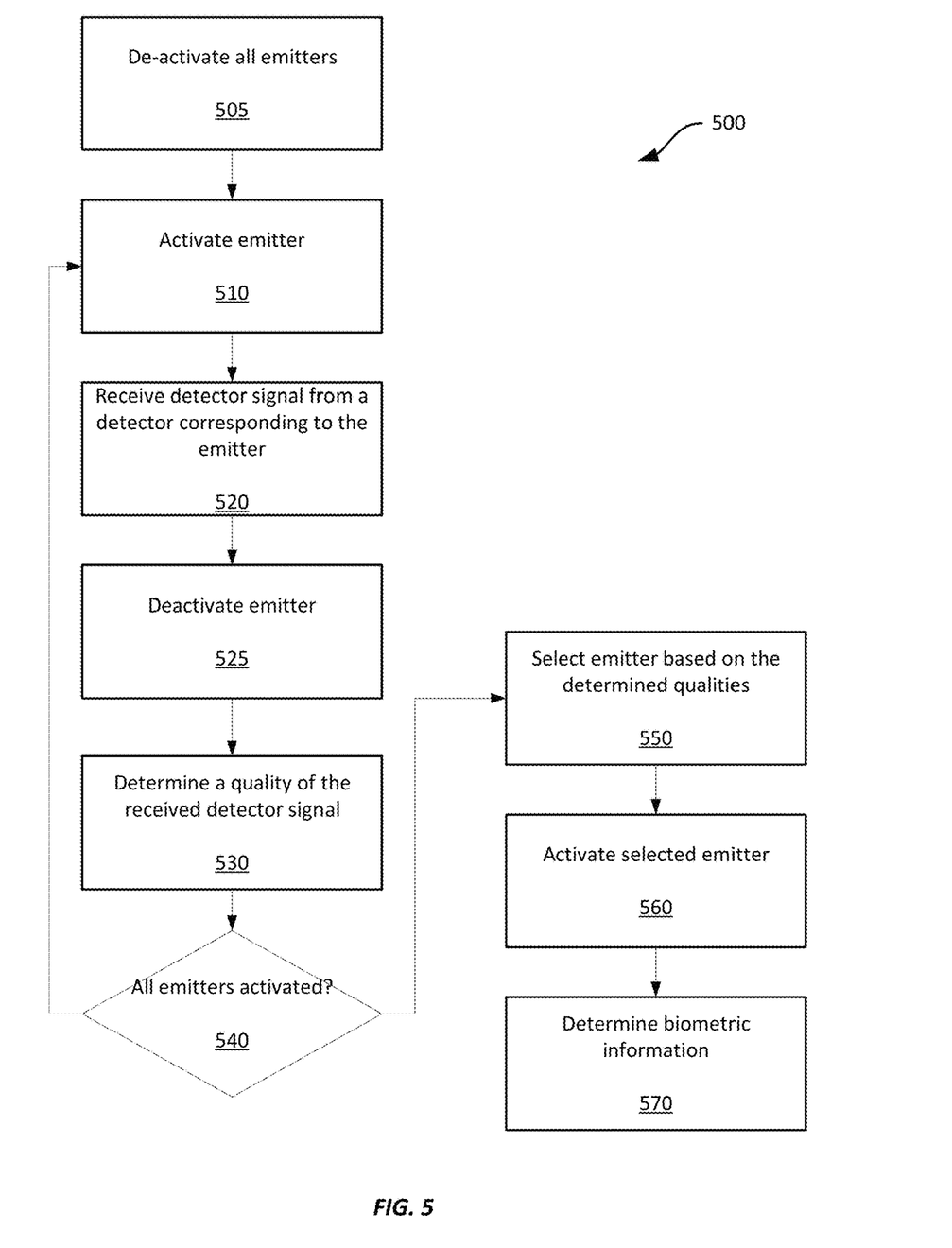
FIG. 5 shows an example method for biometric sensing using a flexible sensing device.

Referring now to FIG. 5, FIG. 5 shows an example method 500 for optimizing a monolithic integrated emitter-detector array in a flexible substrate for biometric sensing. The method 500 will be described with respect to the computing device shown in FIG. 4 and the flexible sensing device shown in FIGS. 1A-1B, however, any suitable flexible sensing device or computing device may be used. The example method 500 shown in FIG. 5 begins in block 505.

At block 505, the computing device 310 first deactivates all emitters. In some examples, a flexible sensing device may include multiple different types of emitters and detectors, e.g., having different colors of EM signals, as discussed above to sense different types of biometric information. In some examples of the method 500, the computing device 310 may separately optimize the different types of emitters and detectors while continuing to operate other types of emitters and detectors normally. Thus, at block 505, the computing device 310 may only deactivate a subset of the emitters, such as the emitters of a particular type, while continuing to use any or all of the remaining emitters normally.

At block 510, the computing device 310 activates a first emitter. To activate an emitter, the processor 410 identifies all available emitters 110a-c and determines which have not yet been activated as a part of the method 500. The processor 410 then selects one of these emitters 120a and transmits a signal to a switch 112a corresponding to the emitter 120a. In this example, the processor 410 selects individual emitters and activates only one; however, in other examples, the flexible sensing device 450 may include one or more scanning circuits having switches corresponding to multiple emitters. In one such example, the processor 410 may then activate and deactivate multiple emitters at a time using a single switch. Or, in some examples, the processor 410 may maintain in memory 420 a data structure indicating a correspondence of emitters and detectors. In one such example, the processor 410 may select detectors one at a time (or a group at a time) and activate all corresponding emitters for the selected detector or group of detectors. In another such example, the processor 410 may select detectors one at a time (or a group at a time), and only activate one corresponding emitter at a time, but step through the remaining corresponding emitters before selecting a new detector.

At block 520, the processor 410 receives a detector signal from a detector corresponding to the activated emitter. In this example, one or more detectors may receive EM signals from the activated emitter. Because the detectors are optically shielded from the emitters, such received EM should mostly be due to reflections of emitted EM signals off of another object, such as a person's skin. As discussed above, a detector, in response to receiving one or more EM signals, generates and transmits a detector signal. The detector circuit carries the sensing signal to the processor 410, which then receives the detector signal. In some examples, more than one detector may receive emitted EM signals and therefore, more than one detector may transmit a detector signal in response to EM signals emitted by the activated emitter. In one such example, the processor 410 may receive such signals one at a time. For example, as discussed above, the processor 410 may selectively activate each detector to selectively receive detector signals form individual detectors. The processor 410, in one such example, may selectively activate and deactivate, in succession, each detector for an activated emitter to attempt to receive detector signals from each detector. Such an example may allow a processor to determine a correspondence between an emitter and one or more detectors. For example, a correspondence may be determined between an emitter and any detector from which a detector signal is received, or from which a detector signal having a quality above a predetermined threshold is received. In some examples, a correspondence between emitters and detectors may be predetermined, thus detector signals may only be received from detectors predetermined to correspond to an activated emitter.

In some examples, detectors in the flexible sensing device 450 may comprise analog detectors that may provide a constant detector signal, such as a voltage, irrespective of any received EM signals. In one such example, the detector may change the voltage of the detector signal based on a strength of a received EM signal, such as an intensity of received light. Such a detector signal may fluctuate over time as the strength of the received EM signal changes over time, e.g., due to movement of the detector, movement of a surface reflecting EM signals from an emitter onto the detector, changes in conditions on a surface reflecting EM signals from an emitter onto the detector, a user's pulse, or other reasons. Such fluctuation may itself be a component of a detector signal, in some examples. For example, a processing device 410 may attempt to determine a pulse rate of a person. Thus, the processing device 410 may receive detector signals over a period of time. Such fluctuations may also include noise, such as due to inherent properties of the detector; EM signals penetrating optical shielding; characteristics of a person's skin; exposure of the detector to other light sources, e.g., sunlight; or movement of the detector. Thus, in some examples, a detector signal may not include an instantaneous or digital signal, but may instead be an analog signal having properties including magnitude, frequency, noise, or other properties.

At block 525, the processor 410 deactivates the activated emitter or emitters.

At block 530, the processor 410 determines a quality of the received detector signal. In this example, the detectors 460 are configured to output detector signals comprising analog voltages based on a strength of a received EM signal. Thus, for each received detector signal, the processor 410 determines a base voltage value for the detector and a magnitude of the received detector signal. In this example, the base voltage for the detector signal is based on a received detector signal during which no emitters are activated. The processor 410 determines a quality based on a difference between the magnitude of the received detector signal and the base voltage. The processor 410 then compares the difference to a predetermined threshold. For example a detector may be configured to output a voltage between 0 and 5 volts. The processor 410 has previously determined that the base voltage output by the detector is 0.3 volts, and a received detector signal has a magnitude of 3.7 volts. Thus, the processor 410 determines a difference of 3.4 volts, which is compared against a threshold. In this example, the predetermined threshold is 3.2 volts, thus the processor 410 determines that the received detector signal is a good detector signal. In some examples, multiple predetermined thresholds may be used, and a quality of a detector signal may be increasingly high the more thresholds the received detector signal meets or exceeds.

In some examples, the processor 410 determines other qualities of the received detector signal. For example, the processor 410 may determine a signal-to-noise (SNR) ratio for a received detector signal. For example, rather than determining the difference between a base output voltage and a voltage of a received detector signal, the processor 410 may determine a ratio between the two voltages. In the example discussed above, the SNR may be computed as 3.7 volts divided 0.3 volts, which results in a SNR of 12.3. In some examples, a SNR may be calculated in decibels, such as by calculating the SNR as described above, calculating the base-10 logarithm of the SNR, and then multiplying that value by 10. Using the example values above, the $SNR_{dB}$ is 10.91. In some examples, the determined SNR may be compared against a threshold or thresholds, as described above, or may be otherwise compared against detector signals received from other detectors. For example, after calculating an $SNR_{dB}$, the processor 410 may determine whether the received detector signal is in the top 10% of received sensor signals that exceed the threshold.

A quality of a received detector signal thus may be established as a SNR, such as a raw SNR or an $SNR_{dB}$. In some examples, a quality may be a binary or otherwise stepped value, such as based on whether the detector signal exceeds one or more threshold values.

Further, as discussed above, the processor 410 may receive detector signals from a plurality of detectors. Thus, in some examples, the processor 410 may determine a quality of a plurality of received detector signals for an activated emitter. The processor 410 determines the qualities of such received detector signals as discussed above.

The processor 410 then stores the determined quality or qualities in the memory 420.

At block 540, the processor 410 determines whether all emitters have been activated. If not, the method 500 returns to block 510. Otherwise, the method proceeds to block 550. However, as discussed above, only a subset of all emitters in a sensing device may be employed with respect to execution of the method 500, thus, at block 540, the processor 410 may determine whether all emitters within the relevant subset have been activated.

At block 550, the processor 410 selects an emitter based on the determined qualities. For example, as discussed above, the processor 410, for each emitter of a plurality of emitters, has determined qualities of received detector signals. Thus, the processor 410 may analyze the determined qualities to identify a highest or best quality detector signal of the determined qualities of all the received detector signals, and select the emitter associated with the highest quality detector signal. For example, an emitter associated with the highest SNR value for a detector signal may be selected. In some examples, however, the processor 410 may analyze the qualities of the detector signals to determine a sum of the qualities for each activated emitter and select the emitter resulting in the highest sum qualities. In some examples, other statistics may be employed.

For example, for each activated emitter, an average value, a range, a standard deviation, a variance, a median value, or other value may be determined to select an emitter. For example an emitter associated with lower peak qualities of received detector signals, but with a mean value above a threshold and a standard deviation below a second threshold may be selected. Such an emitter may be associated with high quality readings from multiple different detectors. In some examples, emitters associated with a lowest range value, but highest peak value, may be selected. In some examples, emitters with a highest mean or median value may be selected. Still other values may be used to select an emitter.

In some examples, the processor 410 may select more than one emitter. For example, multiple emitters may result in high quality detector signals. For example, calculated SNR or $SNR_{dB}$ values for detector signals may be above a threshold value for multiple emitters. In one such example, the processor 410 may select each of such emitters.

At block 560, the processor 410 activates the selected emitter or emitters.

At block 570, the processor determines biometric information, such as a pulse rate, blood oxygen saturation level, blood glucose level, or other biometric information based on received detector signals resulting from the activated selected emitters.

The method 500 of FIG. 5 may be repeated periodically, such as once per minute, to obtain high quality detector signals for determining biometric information. In some examples, the method 500 may be executed in succession, such as based on a flexible sensing device 450 having multiple different types of emitters and detectors. Thus, the method 500 may be executed sequentially, or in parallel, for each different type of emitter.

While the methods and systems herein are described in terms of software executing on various computing devices, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs for editing an image. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes all of the following alternative combinations as appropriate for a particular usage: A alone; B alone; C alone; A and B only; A and C only; B and C only; and A and B and C.

What is claimed is:

1. A monolithic device for sensing biometric information comprising:
   a flexible substrate; and
   a monolithic array of emitters and detectors fabricated in the flexible substrate, the monolithic array comprising:
      a first array of emitters configured to emit first electromagnetic (EM) signals;
      a first array of detectors configured to detect reflections of the first EM signals;
      a first scanning circuit coupled to the first array of emitters, the first scanning circuit configured to selectively activate individual emitters of the first array of emitters; and
      a first sensing circuit coupled to individual detectors of the first array of detectors, the first sensing circuit configured to receive a detection signal from at least one of the detectors of the first array of detectors.

2. The device of claim 1, wherein the first array of emitters comprises a light emitting diode (LED) or an organic LED (OLED).

3. The device of claim 1, wherein the first EM signals comprise red light, orange light, green light, or infrared radiation.

4. The device of claim 1, wherein the first array of detectors comprises a photodiode or a photoresistor.

5. The device of claim 1, further comprising a second array of emitters embedded in the flexible substrate, the second array of emitters configured to emit second electromagnetic (EM) signals, and wherein:
   the first array of detectors is further configured to detect reflections of the second EM signals, and
   the first scanning circuit is further coupled to the second array of emitters and further configured to selectively activate individual emitters of the second array of emitters.

6. The device of claim 1, further comprising:
   a plurality of arrays of emitters,
   a plurality of arrays of detectors, wherein each array of detectors is arranged to correspond with at least one array of emitters.

7. The device of claim 1, wherein the emitters of the first array of emitters are arranged in a regular pattern.

8. The device of claim 7, wherein the regular pattern comprises a rectangular grid or a hexagonal grid.

9. The device of claim 1, wherein the emitters of the first array of emitters are arranged in an irregular pattern.

10. The device of claim 1, further comprising optical shielding between adjacent emitters and detectors of the monolithic array.

11. A system for sensing biometric information comprising:
    a wearable housing;
    a processor and a non-transitory computer-readable medium disposed within the wearable housing, the processor in communication with the non-transitory computer-readable medium and configured to execute program code stored in the non-transitory computer-readable medium;
    a flexible substrate;
    a monolithic sensor fabricated in the flexible substrate in communication with the processor and configured to provide sensor signals to the processor, the sensor comprising:
       a first array of emitters configured to emit first electromagnetic (EM) signals;
       a first array of detectors configured to detect reflections of the first EM signals;
       a first scanning circuit coupled to the first array of emitters, the first scanning circuit configured to selectively activate individual emitters of the first array of emitters; and
       a first sensing circuit coupled to individual detectors of the first array of detectors, the first sensing circuit configured to receive a detection signal from at least one of the detectors of the first array of detectors.

12. The system of claim 11, further comprising a power source in communication with the processor, the non-transitory computer-readable medium, and the sensor.

13. The system of claim 11, wherein the first array of emitters comprises a light emitting diode (LED) or a silicon photodiode.

14. The system of claim 11, wherein the first EM signals comprises red light, orange light, green light, or infrared radiation.

15. The system of claim 11, wherein the first array of detectors comprises a photodiode or a photoresistor.

16. The system of claim 11, further comprising a second array of emitters embedded in the flexible substrate, the second array of emitters configured to emit second electromagnetic (EM) signals, and wherein:
    the first array of detectors is further configured to detect reflections of the second EM signals, and
    the first scanning circuit is further coupled to the second array of emitters and further configured to selectively activate individual emitters of the second array of emitters.

17. The system of claim 11, further comprising:
    a plurality of arrays of emitters,
    a plurality of arrays of detectors, wherein each array of detectors is arranged to correspond with at least one array of emitters.

18. The system of claim 17, wherein emitters of the first array of emitters are arranged in a regular pattern.

19. The system of claim 18, wherein the regular pattern comprises a rectangular grid or a hexagonal grid.

20. The system of claim 17, wherein the emitters of the first array of emitters are arranged in an irregular pattern.

21. The system of claim 11, wherein the wearable housing is configured to be worn on a person's wrist, a person's forearm, a person's upper arm, a person's chest, or a person's leg.

22. The system of claim 11, wherein the processor is further configured to:
cause the first scanning circuit to selectively activate individual emitters of the first array of emitters;
determine biometric information based at least in part on a sensor signal received from the sensor.

23. The system of claim 22, wherein the biometric information comprises one or more of a pulse rate, a blood oxygen saturation level, or a blood glucose level.

24. A method of sensing biometric information using a monolithic sensor comprising:
providing a monolithic array of emitters and detectors fabricated in a flexible substrate, the monolithic array comprising: a first array of emitters, each emitter configured to emit an electromagnetic (EM) signal, a first array of detectors; a first scanning circuit coupled to the first array of emitters, the first scanning circuit configured to selectively activate individual emitters of the first array of emitters; and a first sensing circuit coupled to individual detectors of the first array of detectors, the first sensing circuit configured to receive a detection signal from at least one of the detectors of the first array of detectors;
for each emitter of the monolithic array:
activating the emitter,
receiving a detector signal from one or more detectors of the monolithic array corresponding to the activated emitter,
deactivating the activated emitter, and
determining a quality of the received detector signal;
selecting an emitter based on the determined qualities;
activating the selected emitter; and
determining biometric information based at least in part on a detector signal received from the corresponding detector.

25. The method of claim 24, wherein selecting the emitter comprises:
determining a signal-to-noise ratio (SNR) value of the received detector signal; and
responsive to determining that the SNR value exceeds a threshold SNR value, determining that the SNR value exceeds a threshold value and selecting the emitter associated with the SNR value.

26. The method of claim 24 wherein:
selecting the emitter comprises selecting a plurality of emitters, and
activating the selected emitter comprises activating each emitter of the selected plurality of emitters.

* * * * *